United States Patent
Hilfiger et al.

(10) Patent No.: US 10,934,249 B2
(45) Date of Patent: *Mar. 2, 2021

(54) N-HYDROXYALKYLATED POLYAMINES, METHODS OF MAKING N-HYDROXYALKYLATED POLYAMINES, AND FLUIDS CONTAINING AN N-HYDROXYALKYLATED POLYAMINE

(71) Applicant: Saudi Arabian Oil Company, Dhahran (SA)

(72) Inventors: Matthew Hilfiger, Katy, TX (US); B. Raghava Reddy, Pearland, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/353,607

(22) Filed: Mar. 14, 2019

(65) Prior Publication Data

US 2019/0210956 A1 Jul. 11, 2019

Related U.S. Application Data

(63) Continuation of application No. 16/110,609, filed on Aug. 23, 2018, now Pat. No. 10,343,976, which is a continuation of application No. 15/860,831, filed on Jan. 3, 2018, now Pat. No. 10,131,622.

(51) Int. Cl.
| | |
|---|---|
| *C07C 213/00* | (2006.01) |
| *C09K 8/36* | (2006.01) |
| *C07B 41/02* | (2006.01) |
| *C07C 215/10* | (2006.01) |
| *C07C 215/14* | (2006.01) |
| *C07C 213/04* | (2006.01) |

(52) U.S. Cl.
CPC ............ *C07C 213/00* (2013.01); *C07B 41/02* (2013.01); *C07C 213/04* (2013.01); *C07C 215/10* (2013.01); *C07C 215/14* (2013.01); *C09K 8/36* (2013.01)

(58) Field of Classification Search
None
See application file for complete search history.

(56) References Cited

U.S. PATENT DOCUMENTS

| | | | |
|---|---|---|---|
| 5,254,531 A | 10/1993 | Mueller et al. | |
| 6,339,048 B1 | 1/2002 | Santhanam et al. | |
| 7,345,010 B2 | 3/2008 | Thompson et al. | |
| 7,435,706 B2 | 10/2008 | Mueller et al. | |
| 7,871,962 B2 | 1/2011 | Patel et al. | |
| 8,936,111 B2 | 1/2015 | Maghrabi et al. | |
| 9,469,803 B2 | 10/2016 | Wagle et al. | |
| 10,131,622 B1 | 11/2018 | Hilfiger et al. | |
| 10,343,976 B1 * | 7/2019 | Hilfiger | C07C 213/00 |
| 2005/0159625 A1 | 7/2005 | Coates et al. | |
| 2010/0210480 A1 | 8/2010 | Ballard et al. | |
| 2012/0289437 A1 | 11/2012 | David et al. | |
| 2016/0160112 A1 | 6/2016 | Wagle et al. | |

FOREIGN PATENT DOCUMENTS

| | | | | |
|---|---|---|---|---|
| WO | 2005070873 A2 | 8/2005 | | |
| WO | 2011110803 A1 | 9/2011 | | |
| WO | 2013169402 A1 | 11/2013 | | |
| WO | 2014039410 A1 | 3/2014 | | |
| WO | 2015006101 A1 | 1/2015 | | |
| WO | WO-2018143923 A1 * | 8/2018 | ........... | C07C 218/14 |

OTHER PUBLICATIONS

International Search Report and Written Opinion dated Feb. 18, 2019 pertaining to International Application No. PCT/US2018/067162 filed Dec. 21, 2018, 14 pgs.

* cited by examiner

*Primary Examiner* — Amy C Bonaparte
(74) *Attorney, Agent, or Firm* — Dinsmore & Shohl LLP

(57) ABSTRACT

N-hydroxyalkylated polyamines, methods of making N-hydroxyalkylated polyamines, and drilling fluids containing N-hydroxyalkylated polyamines are provided, in which the N-hydroxyalkylated polyamine includes Formula (I):

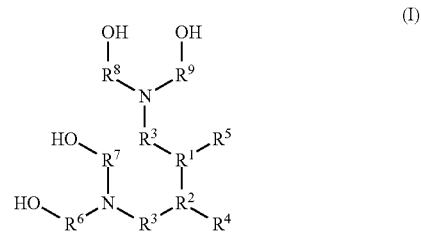

where $R^1$ and $R^2$ are independently a —C or —CH group; $R^3$ is an aliphatic hydrocarbyl; $R^4$ and $R^5$ are independently acyclic hydrocarbyls, or $R^1$, $R^2$, $R^4$, and $R^5$ are covalently connected to form a cyclic hydrocarbyl; and $R^6$, $R^7$, $R^8$, and $R^9$ are independently acyclic hydrocarbyls or acyclic heterohydrocarbyls.

11 Claims, No Drawings

N-HYDROXYALKYLATED POLYAMINES, METHODS OF MAKING N-HYDROXYALKYLATED POLYAMINES, AND FLUIDS CONTAINING AN N-HYDROXYALKYLATED POLYAMINE

CROSS-REFERENCE TO RELATED APPLICATIONS

This application is a continuation of U.S. application Ser. No. 16/110,609 filed Aug. 23, 2018, which is a continuation of U.S. application Ser. No. 15/860,831 filed Jan. 3, 2018 now U.S. Pat. No. 10,131,622, which is incorporated by reference in its entirety in this disclosure.

TECHNICAL FIELD

Embodiments of the disclosure relate to N-hydroxyalkylated polyamines, methods of making N-hydroxyalkylated polyamines, and fluids containing an N-hydroxyalkylated polyamine.

BACKGROUND

Drilling fluids in the oil and gas industries perform a myriad of tasks, including cleaning wells, holding cuttings in suspension, reducing friction, lubricating drilling tools, maintaining stability of wellbores, and preventing fluid loss. The drilling fluids must be viscous to suspend cuttings in the fluid, and must have control of this viscosity over a broad temperature range, as oil and gas wells can be located in a multitude of diverse locations, for example, conditions of from less than 0° C. in freezing permafrost zones to temperatures exceeding 400° C. in geothermal wells.

Surfactants can be added to fluids as rheology modifiers to ensure performance of these tasks. A surfactant refers to a compound that reduces the surface tension or interfacial tension between two or more liquids or between a liquid and a solid. Surfactants may provide improved performance, including rheological performance, as additives in various fluids, such as drilling fluids, cleaning solutions, paints and coatings, corrosion inhibitors, and personal care formulations. Conventional surfactants include dimer diamines, dimer diacids, and esters of dimer acids. However, these compounds do not perform well over a broad temperature range and are difficult to synthesize.

SUMMARY

Accordingly, an ongoing need exists for compounds that provide improved rheological properties for wellbore fluids over a broad range of temperatures. Moreover, an ongoing need exists for methods of synthesizing compounds that have improved rheological properties over a broad temperature range. The present embodiments address these needs by providing N-hydroxyalkylated polyamines, methods of making N-hydroxyalkylated polyamines, and fluids containing an N-hydroxyalkylated polyamine that allow for improved rheological properties over a broad temperature range.

In one embodiment, the present disclosure relates to an N-hydroxyalkylated polyamine comprising Formula (I):

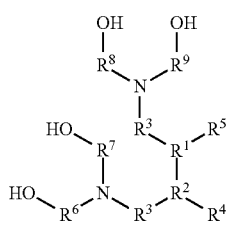

where $R^1$ and $R^2$ are independently a —C or —CH group; $R^3$ is an aliphatic hydrocarbyl; $R^4$ and $R^5$ are independently acyclic hydrocarbyls, or $R^1$, $R^2$, $R^4$, and $R^5$ are covalently connected to form a cyclic hydrocarbyl; and $R^6$, $R^7$, $R^8$, and $R^9$ are independently acyclic hydrocarbyls or acyclic heterohydrocarbyls.

Another embodiment of the present disclosure relates to a method of making an N-hydroxyalkylated polyamine by reacting a polyamine having Formula (XXIV):

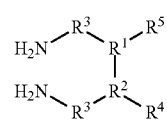

with a cyclic oxide to produce the N-hydroxyalkylated polyamine, where $R^1$ and $R^2$ are independently a —C or —CH group; $R^3$ is an aliphatic hydrocarbyl; $R^4$ and $R^5$ are independently acyclic hydrocarbyls, or are covalently connected to form a cyclic hydrocarbyl.

Another embodiment of the present disclosure relates to a drilling fluid containing an aqueous phase, an oleaginous phase, and an N-hydroxyalkylated polyamine comprising Formula (I):

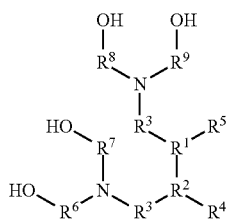

where $R^1$ and $R^2$ are independently a —C or —CH group; $R^3$ is an aliphatic hydrocarbyl; $R^4$ and $R^5$ are independently acyclic hydrocarbyls, or $R^1$, $R^2$, $R^4$, and $R^5$ are covalently connected to form a cyclic hydrocarbyl; and $R^6$, $R^7$, $R^8$, and $R^9$ are independently acyclic hydrocarbyls or acyclic heterohydrocarbyls.

Additional features and advantages of the described embodiments will be set forth in the detailed description which follows, and in part will be readily apparent to those skilled in the art from that description or recognized by practicing the described embodiments, including the detailed description which follows as well as the claims.

DETAILED DESCRIPTION

Specific embodiments of the present application will now be described. The disclosure may, however, be embodied in different forms and should not be construed as limited to the embodiments set forth in this disclosure. Rather, these embodiments are provided so that this disclosure will be thorough and complete, and will fully convey the scope of the subject matter to those skilled in the art.

Unless otherwise defined, all technical and scientific terms used in this disclosure have the same meaning as commonly understood by one of ordinary skill in the art. The terminology used in the description is for describing particular embodiments only and is not intended to be limiting.

As used in the specification and appended claims, the singular forms "a," "an," and "the" are intended to include the plural forms as well, unless the context clearly indicates otherwise.

The disclosure of any ranges in the specification and claims are to be understood as including the range itself and also anything subsumed within the range, as well as endpoints. Unless otherwise indicated, the numerical properties set forth in the specification and claims are approximations that may vary depending on the desired properties sought to be obtained in embodiments of the present disclosure. Notwithstanding that numerical ranges and parameters setting forth the broad scope of this disclosure are approximations, the numerical values set forth in the specific examples are reported as precisely as possible. Any numerical values, however, may inherently contain certain errors necessarily resulting from error in their respective measurements or resulting from clerical error.

As used in this disclosure, a "hydrocarbyl" refers to a chemical composition consisting of carbon and hydrogen. Typically, a hydrocarbyl group is a radical analogous to a hydrocarbon molecule with a single missing hydrogen (where the hydrocarbyl group is connected to another chemical group). As used in this disclosure, a "heterohydrocarbyl" refers to a hydrocarbon composition in which one or more carbon atoms are replaced with a heteroatom, such as O, S, N, P, or combinations of these.

As used in this disclosure, "aliphatic" refers to an acyclic or cyclic, saturated or unsaturated carbon compound, which is not aromatic. Further, as used in this disclosure, "aliphatic hydrocarbyl" refers to an acyclic or cyclic, saturated or unsaturated compound consisting of carbon and hydrogen, which is not aromatic.

As used in this disclosure, "acyclic," such as "acyclic hydrocarbon," "acyclic hydrocarbyl," or "acyclic heterohydrocarbyl," refers to hydrocarbon moiety whose atoms do not form a ring. Conversely, as used in this disclosure, "cyclic hydrocarbyl" refers to an aromatic or aliphatic hydrocarbon moiety with at least one ring or cyclic moiety in its structural backbone, for example, aryl or cycloalkyl moieties.

As used in this disclosure, "saturated," refers to a hydrocarbon moiety containing carbon atoms connected by single bonds, which does not contain double or triple carbon-carbon bonds. Typically, a saturated hydrocarbyl group may be analogous to an alkane with a single missing hydrogen (where the alkane is connected to another chemical group). Conversely, as used in this disclosure, "unsaturated," refers to a hydrocarbon moiety containing at least one carbon-carbon double or triple bond. Typically, an unsaturated hydrocarbyl group may be analogous to an alkene or alkyne with a single missing hydrogen (where the alkene or alkyne is connected to another chemical group).

As used throughout the disclosure, "aqueous phase" refers to a fluid containing water. Similarly, "oleaginous phase" refers to a fluid containing, resembling, or having the properties of oil. As used in this disclosure, "oil," refers to a hydrocarbon-containing liquid derived from petroleum.

The term "clay," as used in this disclosure, refers to a material that is plastic upon wetting and hardened upon drying, containing hydrous aluminum phyllosilicates, including but not limited to talc and montmorillonite clays, such as kaolin, bentonite, and barite.

As used in this disclosure, "N-hydroxyalkylated polyamine" refers to a chemical compound having at least two nitrogen atoms, with each nitrogen atom being bonded to two hydroxyalkyl groups; thereby the composition has at least 4 hydroxyl moieties.

As previously stated, an ongoing need exists for compounds which provide improved rheological properties of wellbore fluids over a broad range of temperatures, and for methods of synthesizing compounds and fluids containing the compound. The present embodiments may address these needs by providing N-hydroxyalkylated polyamines, methods of making N-hydroxyalkylated polyamines, and fluids containing an N-hydroxyalkylated polyamine. As compared to conventional drilling fluids, fluids containing the N-hydroxyalkylated polyamine of the present disclosure may have improved electrical stability, while maintaining comparable gel strength and shear stress. Additionally, fluids containing the N-hydroxyalkylated polyamine of the present disclosure may have improved shear stress at reduced revolutions per minute (rpm), such as 3 rpm, and high temperatures, such as at or greater than 300° F., as compared to conventional drilling fluids that do not contain the N-hydroxyalkylated polyamine.

One embodiment of the present disclosure is directed to N-hydroxyalkylated polyamides in accordance with Formula (I):

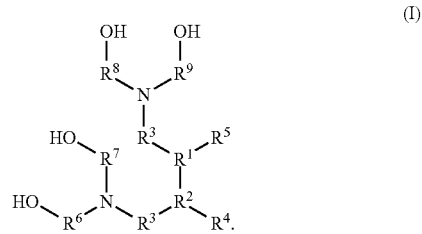

In Formula (I), $R^1$ and $R^2$ are independently a —C or —CH group; $R^3$ is an aliphatic hydrocarbyl; $R^4$ and $R^5$ are independently acyclic hydrocarbyls, or $R^1$, $R^2$, and $R^5$ are covalently connected to form a cyclic hydrocarbyl; and $R^6$, $R^7$, $R^8$, $R^9$ are independently acyclic hydrocarbyls or acyclic heterohydrocarbyls.

As previously stated, $R^3$ is an aliphatic hydrocarbyl. $R^3$ may be a saturated or unsaturated aliphatic hydrocarbyl. In some embodiments, $R^3$ may be a saturated or unsaturated acyclic hydrocarbyl. In some particular embodiments, $R^3$ may be a saturated aliphatic hydrocarbyl, such as a saturated acyclic hydrocarbyl. In one or more embodiments, $R^3$ is a saturated or unsaturated $C_2$-$C_{20}$ aliphatic hydrocarbyl group ($C_2$-$C_{20}$ refers to a group having from 2 to 20 carbons). In specific embodiments, $R^3$ is a saturated or unsaturated $C_2$-$C_{20}$ aliphatic hydrocarbyl group, or a saturated or unsaturated $C_2$-$C_{12}$ aliphatic hydrocarbyl group, or a saturated $C_5$-$C_{10}$ aliphatic hydrocarbyl group. In a specific embodiment, $R^3$ is a saturated aliphatic hydrocarbyl. In one or more embodiments, $R^3$ may be a saturated or unsaturated $C_2$-$C_{20}$ acyclic hydrocarbyl group, or a saturated or unsaturated $C_2$-$C_{12}$ acyclic hydrocarbyl group, or a saturated $C_5$-$C_{10}$ acyclic hydrocarbyl group.

In some embodiments, at least one of $R^4$ and $R^5$ may independently be $C_2$-$C_{20}$ acyclic hydrocarbyls, or $C_5$-$C_{15}$ acyclic hydrocarbyls, or $C_6$-$C_{12}$ acyclic hydrocarbyls. In one or more embodiments, at least one of $R^4$ and $R^5$ may independently be an unsaturated $C_2$-$C_{20}$ acyclic hydrocarbyls. In other embodiments, both $R^4$ and $R^5$ are unsaturated $C_2$-$C_{20}$ acyclic hydrocarbyls. In another embodiment, the $R_3$ is saturated $C_5$-$C_{30}$ acyclic hydrocarbyls, and $R^4$ and $R^5$ independently are $C_5$-$C_{15}$ acyclic hydrocarbyl chains.

In one or more embodiments, $R^4$ and $R^5$ of the N-hydroxyalkylated polyamine of Formula (I), in cooperation with the $R^1$ and $R^2$, may form saturated or unsaturated cyclic hydrocarbyls. Various aromatic or cyclic moieties are considered suitable cyclic hydrocarbyls. In one or more embodiments, the cyclic hydrocarbyls may be selected from cyclohexane, cyclohexane, benzene, naphthalene, or decahydronapthalene. In further embodiments, the cyclic hydrocarbyls may be substituted with alkyl, aminoalkyl, aminoalkoxy, hydroxyl, alkoxyl, alkylthio, amino, halo, haloalkyl, silyl, phosphoryl, sulfonyl, or combinations thereof. In other embodiments, the cyclic hydrocarbyls may be substituted with at least one saturated or unsaturated. $C_2$-$C_{20}$ acyclic hydrocarbyls. In further embodiments, the cyclic hydrocarbyls are substituted with at least two acyclic hydrocarbyls.

In yet another embodiment, the cyclic hydrocarbyls are substituted with at least one $C_2$-$C_{20}$ aminoalkoxy comprising two terminal hydroxyls. In one or more embodiments, the cyclic hydrocarbyls are selected from Formulas (II) to (XVIII):

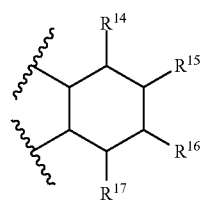
(II)

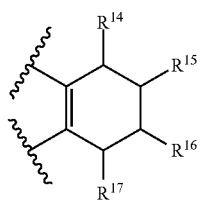
(III)

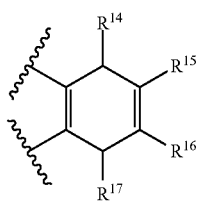
(IV)

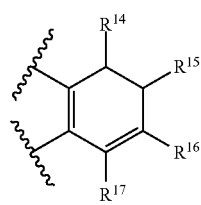
(V)

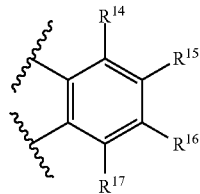
(VI)

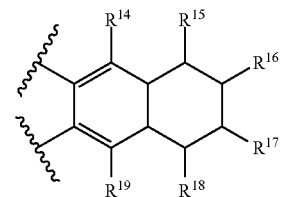
(VII)

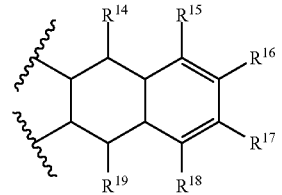
(VIII)

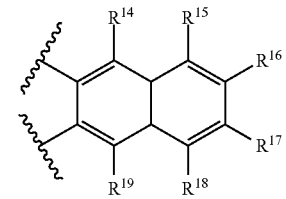
(IX)

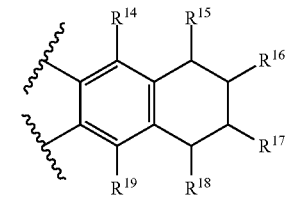
(X)

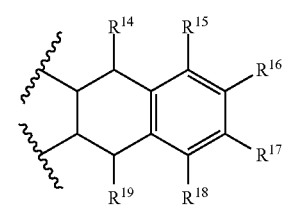
(XI)

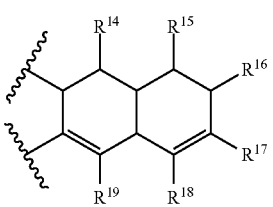

(XII)

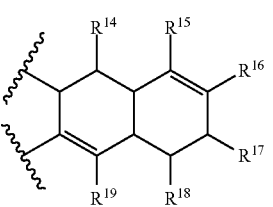

(XIII)

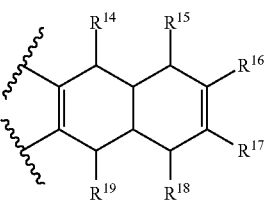

(XIV)

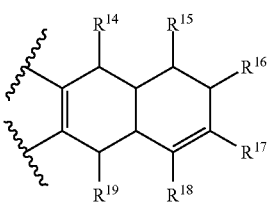

(XV)

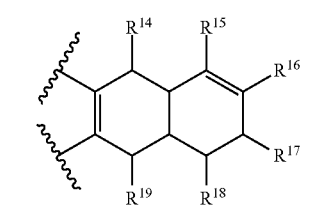

(XVI)

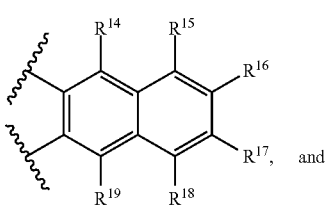

(XVII)

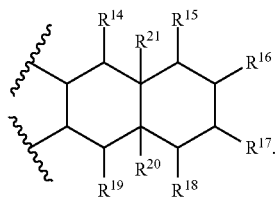

(XVIII)

In Formulas (II) to (XVIII), $R^{14}$, $R^{15}$, $R^{16}$, $R^{17}$, $R^{18}$, $R^{19}$, $R^{20}$, and $R^{21}$ (where applicable) independently are H, alkyl, aminoalkyl, aminoalkoxy, hydroxyl, alkoxyl, alkylthio, amino, halo, haloalkyl, silyl, phosphoryl, sulfonyl, or combinations of these. Any of the R groups $R^{14}$, $R^{15}$, $R^{16}$, $R^{17}$, $R^{18}$, $R^{19}$, $R^{20}$, and $R^{21}$ (where applicable), may be a hydrogen, a saturated aliphatic hydrocarbyl group that is unsubstituted, or a saturated aliphatic hydrocarbyl group substituted with one or more hydroxyl, aminoalkoxy, alkoxyl, alkylthio, amino, halo, haloalkyl, silyl, phosphoryl, or sulfonyl groups. In some particular embodiments, any of $R^{14}$, $R^{15}$, $R^{16}$, $R^{17}$, $R^{18}$, $R^{19}$, $R^{20}$, and $R^{21}$ (where applicable) may be may be a saturated or an unsaturated acyclic hydrocarbyl group that is unsubstituted or substituted with one or more hydroxyl, aminoalkoxy, alkoxyl, alkylthio, amino, halo, haloalkyl, silyl, phosphoryl, or sulfonyl groups. In some embodiments one or more of $R^{14}$, $R^{15}$, $R^{16}$, $R^{17}$, $R^{18}$, $R^{19}$, $R^{20}$, and $R^{21}$ independently may comprise aminoalkyl moieties, such as aminoalkoxyl moieties.

In the formulas, a wavy line "∿∿" at the end of a bond refers to an open covalent bond, which may be a single, double, or even a triple bond between that constituent and the fragment of a molecule not shown (such as $R^1$ and $R^2$). In some embodiments, one or more of $R^{14}$, $R^{15}$, $R^{16}$, $R^{17}$, $R^{18}$, $R^{19}$, $R^{20}$, and $R^{21}$ independently may contain from 1 to 100 carbons, such as from 1 to 50, 1 to 25, or 1 to 10 carbons. $R^{14}$, $R^{15}$, $R^{16}$, $R^{17}$, $R^{18}$, $R^{19}$, $R^{20}$, and $R^{21}$ independently may contain at least one unsaturated hydrocarbyl. In one or more embodiments, the hydrocarbyl moiety may include the formula $C_nH_{2n}$, $C_nH_{2n-2}$, $(C_nH_{2n}O)_xC_nH_{2n}$, $(C_nH_{2n-2}O)_xC_nH_{2n}$, or $(C_nH_{2n-2}O)_xC_nH_{2n-2}$, where n is an integer from 2 to 20 and x is an integer from 1 to 10.

Referring again to Formula (I), $R^6$, $R^7$, $R^8$, and $R^9$ are independently acyclic hydrocarbyls, or acyclic heterohydrocarbyls. In one or more embodiments, $R^6$, $R^7$, $R^8$, and $R^9$ independently may be saturated or unsaturated straight chain or branched acyclic hydrocarbyls. For example and not by way of limitation, $R^6$, $R^7$, $R^8$, and $R^9$ independently may include a hydrocarbyl moiety having the formula $C_nH_{2n}$, $C_nH_{2n-2}$, $(C_nH_{2n}O)_xC_nH_{2n}$, $(C_nH_{2n-2}O)_xC_nH_{2n}$, or $(C_nH_{2n-2}O)_xC_nH_{2n-2}$, where n is an integer from 2 to 20 and x is an integer from 1 to 10.

In one or more additional embodiments, $R^6$, $R^7$, $R^8$, and $R^9$ independently may be saturated or unsaturated straight chain or branched acyclic heterohydrocarbyls. For example, $R^6$, $R^7$, $R^8$, and $R^9$ independently may include a heterohydrocarbyl having the formula $(C_nH_{2n-2}O)_xC_nH_{2n}$, $(C_nH_{2n-2}O)_xC_nH_{2n-2}$. In some particular embodiments, n may be an integer from 2 to 10, such as from 2 to 5, or 2 to 4. Additionally or alternatively, in some particular embodiments, x may be an integer from 1 to 10, 1 to 5, 1 to 4, 2 to 5, 2 to 10, or 4 to 10.

In one or more embodiments, the N-hydroxyalkylated polyamine may include at least one of Formulas (XIX) to (XXIII):

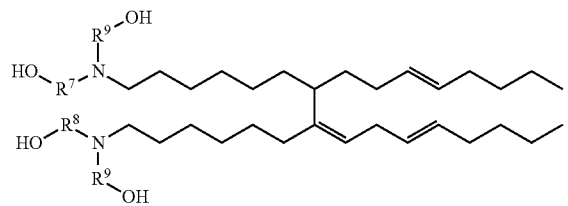
(XIX)
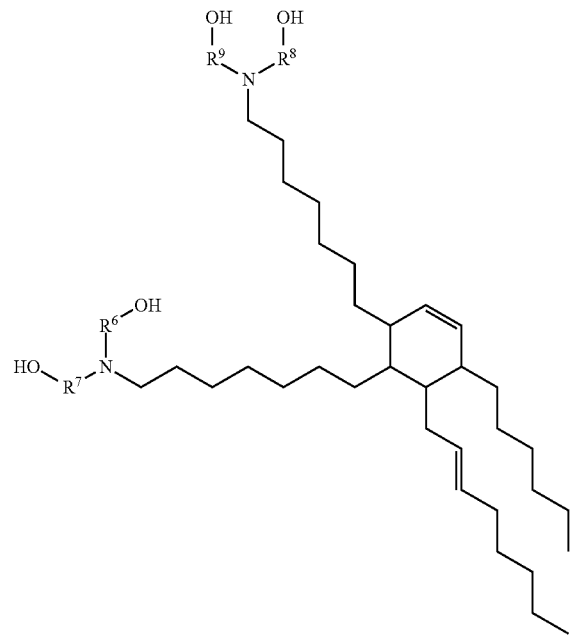
(XX)
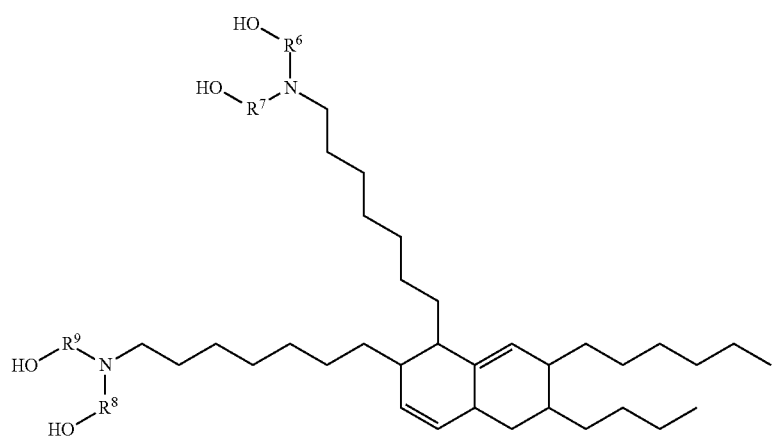
(XXI)

(XXII)

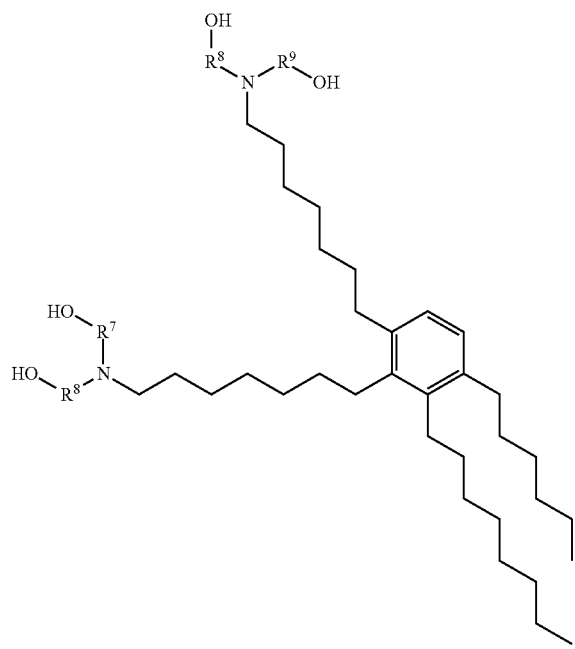

(XXIII)

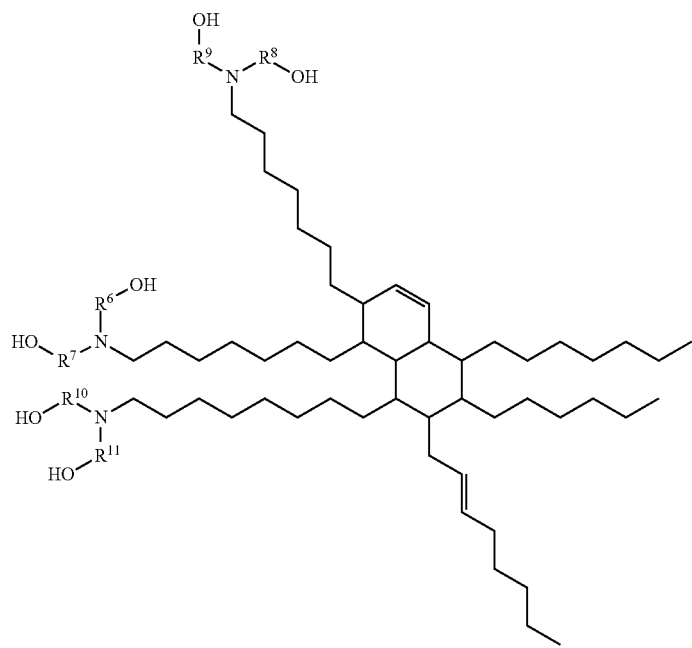

In Formulas (XIX) to (XVIII), $R^6$, $R^7$, $R^8$, $R^9$, and, where applicable, $R^{10}$ and $R^{11}$ are independently acyclic hydrocarbyls or acyclic heterohydrocarbyls. In one or more embodiments, $R^6$, $R^7$, $R^8$, $R^9$, $R^{10}$, and $R^{11}$ independently may be saturated or unsaturated straight chain or branched acyclic hydrocarbyls. For example and not by way of limitation, $R^6$, $R^7$, $R^8$, $R^9$, $R^{10}$, and $R^{11}$ independently may include a hydrocarbyl moiety having the formula $C_nH_{2n}$, $C_nH_{2n-2}$, $(C_nH_{2n}O)_xC_nH_{2n}$, $(C_nH_{2n-2}O)_xC_nH_{2n}$, or $(C_nH_{2n-2}O)_xC_nH_{2n-2}$, where n is an integer from 2 to 20 and x is an integer from 1 to 10. In one or more additional embodiments, $R^6$, $R^7$, $R^8$, $R^9$, $R^{10}$, and $R^{11}$ independently may be saturated or unsaturated, straight chain or branched acyclic heterohydrocarbyls. For example, $R^6$, $R^7$, $R^8$, $R^9$, $R^{10}$, and $R^{11}$ independently may include a heterohydrocarbyl having the formula $(C_nH_{2n-2}O)_xC_nH_{2n}$, $(C_nH_{2n-2}O)_xC_nH_{2n-2}$. In some particular embodiments, n may be an integer from 2 to 10, such as from 2 to 5, or 2 to 4. Additionally or alternatively, in some particular embodiments, x may be an integer from 1 to 10, 1 to 5, 1 to 4, 2 to 5, 2 to 10, or 4 to 10.

Further embodiments of the present disclosure include methods of making an N-hydroxyalkylated polyamine by reacting the polyamine of Formula (XXIV) with cyclic oxide.

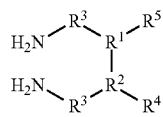
(XXIV)

In Formula (XXIV), $R^1$-$R^5$ may be in accordance with any of the embodiments previously described.

In one or more embodiments, the polyamine may have at least one of Formulas (XXV) to (XXIX):

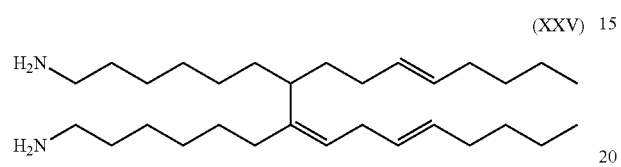
(XXV)

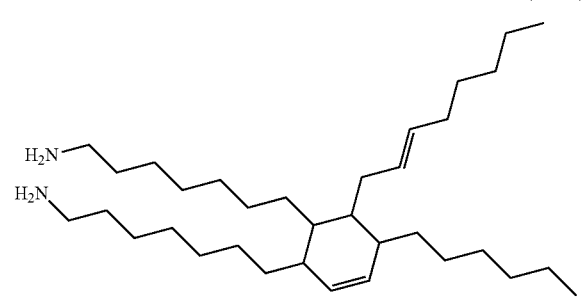
(XXVI)

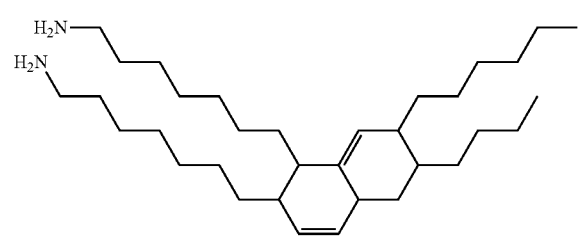
(XXVII)

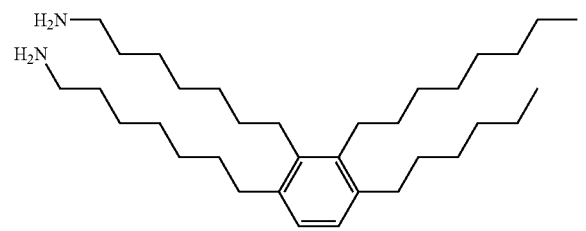
(XXVIII)

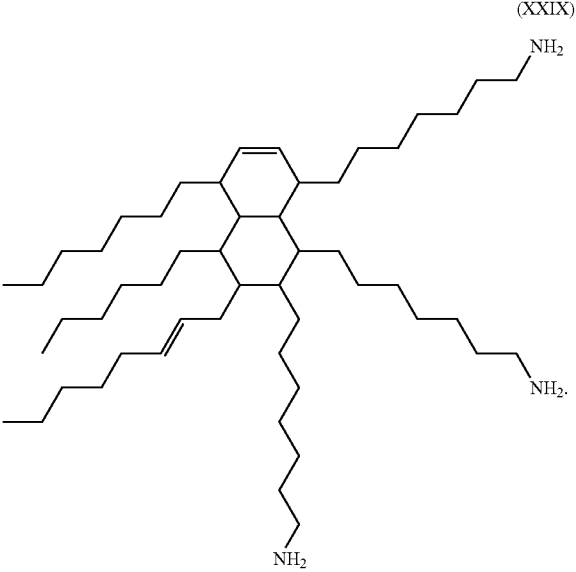
(XXIX)

In one or more embodiments, the reacting step may be a ring opening epoxide reaction. Without being bound by any particular theory, the primary amino moieties present in Formula (XXIV) may cause the ring of the cyclic oxide to open by nucleophilic substitution, hydroxyalkylating the amino group to produce an N-hydroxyalkylated polyamine, such as the N-hydroxyalkylated polyamine of Formula (I).

Any suitable cyclic oxide or mixture of cyclic oxides may be utilized in this reaction step. As non-limiting examples, suitable cyclic oxides may include ethylene oxide, propylene oxide, butene monoxide, dodecene monoxide, isobutylene monoxide, styrene oxide, 1,2-diisobutylene oxide, 2,3-diisobutylene oxide, phenyl glycidyl ether, allyl glycidyl ether, methyl glycidyl ether, ethyl glycidyl ether, vinyl cyclohexene monoxide, butadiene dioxide, 3-methyl-3,4-epoxy butene-1, butadiene monoxide, vinyl cyclohexene dioxide, glycidyl methacrylate, epichlorohydrin, dicyclopentadiene monoxide, limonene dioxide, isoprene monoxide, oxetane, diglycidyl ether of pentanediol, bis 1,1'-(3,4-epoxy-6-methyl phenyl) methyl formate, the reaction product of the diglycidyl ether of pentanediol and bisphenol A, 3,3-dimethyl oxetane, 1-epoxy ethyl-3,4-epoxy cyclohexane, 3,3-diethyl oxetane, 3-ethyl-3 butyl oxetane, 3-chloro-methyl-3-methyl oxetane, 3-methyl-2-ethyl oxetane, 1,4-dichloro-2,3-epoxy butane, allyl epoxy stearate, and other cyclic oxides. In some particular embodiments, the cyclic oxide may be ethylene oxide, butylene oxide, propylene oxide, or combinations of these. In some embodiments, the cyclic oxide may be ethylene oxide.

Without being bound by any particular theory, the N-hydroxyalkylated polyamine may function as a surfactant, meaning that it may reduce the surface tension between two liquids or between a liquid and a solid. Moreover, the N-hydroxyalkylated polyamine may additionally or alternatively be amphiphilic, meaning that it may have a lipophilic tail (the non-polar R groups) and one or more hydrophilic heads (polar —OH groups). These properties may be beneficial for use as an additive in many industries, including but not limited to drilling fluids, cleaning solutions, paints and coatings, corrosion inhibitors, and personal care formulations.

In conventional methods, dimer diamines or dimer diacids may be used to provide improved rheological properties in fluids. However, without being bound by any particular theory, the N-hydroxyalkylated polyamine of the present disclosure may provide an unexpectedly improved rheology when added to fluids as compared to conventional drilling fluids. Specifically, the N-hydroxyalkylated polyamine achieves additional benefits, such as improved viscosity at increased temperatures and reduced shear, such as, for instance, 3 rpm and at least 300° F., as compared to conventional drilling fluids. Moreover, typically the synthesis of conventional drilling fluid requires use of catalysts (such as KOH or NaOH) and often heat (such as greater than 100° C.). These catalysts create a basic environment that allows the compound to indefinitely react with a cyclic oxide (such as epoxide), until the reactive sites become too diluted to further react, or until all of the added cyclic oxide is consumed. Unlike conventional methodology, the methods of the present disclosure may not require use of a catalyst. Instead, without being bound by any particular theory, the nucleophilic nature of the amine in Formula (XXIV) may open the ring of the cyclic oxide, eliminating the need for additional catalysts.

Furthermore, the methods of the present disclosure are, in some embodiments, self-limiting. In one or more embodiments, excess cyclic oxide may be mixed with the polyamine to produce a determinate number of moles of the N-hydroxyalkylated polyamine despite the number of moles of cyclic oxide added to the polyamine.

In other embodiments, the method may further involve use of a catalyst to further alkoxylate the polyamine. As mentioned, use of a catalyst, including but not limited to KOH and NaOH, may allow hydroxyalkylation to initiate and continue until all reactive sites have reacted. However, without being bound by any particular theory, when a catalyst, such as KOH or NaOH is used, the reaction may not be as efficient, and intermediary compounds may be formed. For example, the amino moieties may not be fully hydroxyalkylated, resulting in a partial N-hydroxyalkylated polyamine in which one or both of the amino groups may be partially hydroxyalkylated, or may not be hydroxyalkylated. One possible intermediary structure includes but is not limited in any way to Formula XXX:

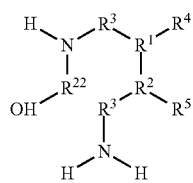

XXX

In Structure XXX, $R^1$, $R^2$, $R^3$, $R^5$ and $R^6$ are in accordance with any of the previously-described embodiments. $R^{22}$ is a hydrogen, or a saturated or unsaturated aliphatic hydrocarbyl group that is unsubstituted or is substituted with one or more hydroxyl, aminoalkoxy, alkoxyl, alkylthio, amino, halo, haloalkyl, silyl, phosphoryl, or sulfonyl groups. $R^{22}$ may be acyclic hydrocarbyls or acyclic heterohydrocarbyls. In some embodiments, $R^{22}$ may be saturated or unsaturated straight chain or branched acyclic hydrocarbyls. In some particular embodiments, $R^{22}$ may include a hydrocarbyl or heterohydrocarbyl moiety having the formula $C_nH_{2n}$, $C_nH_{2n-2}$, $(C_nH_{2n}O)_xC_nH_{2n}$, $(C_nH_{2n-2}O)_xC_nH_{2n}$, or $(C_nH_{2n-2}O)_xC_nH_{2n-2}$, where n is an integer from 2 to 20 and x is an integer from 1 to 10. In other embodiments, n may be an integer from 2 to 10, such as from 2 to 5, or 2 to 4. Additionally or alternatively, in some particular embodiments, x may be an integer from 1 to 10, 1 to 5, 1 to 4, 2 to 5, 2 to 10, or 4 to 10.

Additional non-limiting and non-exhaustive examples of intermediary compounds include those in accordance with Formula XXXI, XXXII, and XXXIII.

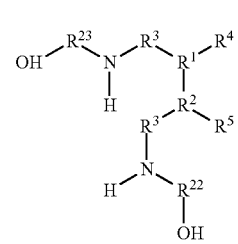

XXXI

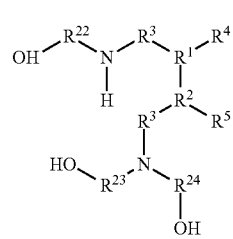

XXXII

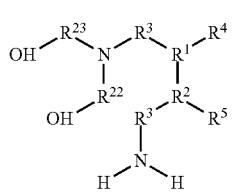

XXXIII

In Formula XXXI, XXXII and XXXIII, $R^1$, $R^2$, $R^3$, $R^4$ and $R^5$ are in accordance with any embodiments previously described. Additionally, $R^{22}$, $R^{23}$, and $R^{24}$ (when present), are also in accordance with any embodiments previously described. $R^{22}$, $R^{23}$, and $R^{24}$ (when present), may be a hydrogen, or a saturated or unsaturated aliphatic hydrocarbyl group that is unsubstituted or is substituted with one or more hydroxyl, aminoalkoxy, alkoxyl, alkylthio, amino, halo, haloalkyl, silyl, phosphoryl, or sulfonyl groups. $R^{22}$, $R^{23}$, and $R^{24}$ (when present) may be acyclic hydrocarbyls or acyclic heterohydrocarbyls. In some embodiments, $R^{22}$, $R^{23}$, and $R^{24}$ (when present) may be saturated or unsaturated straight chain or branched acyclic hydrocarbyls. In some particular embodiments, $R^{22}$, $R^{23}$, and $R^{24}$ (when present) may include a hydrocarbyl or heterohydrocarbyl moiety having the formula $C_nH_{2n}$, $C_nH_{2n-2}$, $(C_nH_{2n}O)_xC_nH_{2n}$, $(C_nH_{2n-2}O)_xC_nH_{2n}$, or $(C_nH_{2n-2}O)_xC_nH_{2n-2}$, where n is an integer from 2 to 20 and x is an integer from 1 to 10. In other embodiments, n may be an integer from 2 to 10, such as from 2 to 5, or 2 to 4. Additionally or alternatively, in some particular embodiments, x may be an integer from 1 to 10, 1 to 5, 1 to 4, 2 to 5, 2 to 10, or 4 to 10.

It should be understood that these structures are intended to include isomers (both constitutional and stereoisomers), such that $R^1$ may be fully hydroxyalkoxylated (two hydroxyl groups bonded to the amino moiety) or partially hydroxyalkoxylated (one hydroxyl group bonded to the amino moiety), while $R^2$ is partially hydroxyalkoxylated (one hydroxyl group bonded to the amino moiety) or is unhydroxyalkoxylated (no hydroxyl groups bonded to the amino moiety), or alternatively, $R^2$ may be fully hydroxyalkoxylated (two hydroxyl groups bonded to the amino moiety) or partially hydroxyalkoxylated (one hydroxyl group bonded to the amino moiety), while $R^1$ is partially hydroxyalkoxylated (one hydroxyl group bonded to the amino moiety) or is unhydroxyalkoxylated (no hydroxyl groups bonded to the amino moiety).

In some embodiments, these intermediary structures may constitute less than or equal to 30 weight percent (wt %) of the total N-hydroxyalkylated polyamine product. For instance, the intermediary structures may constitute less than or equal to 20 wt %, 10 wt %, 5 wt %, or 3 wt % of the total N-hydroxyalkylated polyamine product.

Further embodiments of the disclosure are also directed to drilling fluids containing an aqueous phase, an oleaginous phase, and an N-hydroxyalkylated polyamine. The N-hydroxyalkylated polyamine may be in accordance with any of the previously-described embodiments. In some embodiments, the drilling fluid may also contain the intermediary products previously discussed. Again, these intermediary structures may constitute less than or equal to 30 wt % of the total N-hydroxyalkylated polyamine product. For instance, the intermediary structures may constitute less than or equal to 20 wt %, 10 wt %, 5 wt %, or 3 wt % of the total N-hydroxyalkylated polyamine product in the drilling fluid.

The aqueous phase may contain water, including freshwater or seawater. The aqueous phase may contain brine, including natural and synthetic brine, such as saturated brine, or brackish water. The aqueous phase in some embodiments may use water containing organic compounds or salt. Without being bound by any particular theory, salt or other organic compounds may be incorporated into the aqueous phase to control the density of the drilling fluid. Increasing the saturation of the aqueous phase by increasing the salt concentration or the level of other organic compounds in the aqueous phase may increase the density of the drilling fluid. Suitable salts include but are not limited to alkali metal chlorides, hydroxides, or carboxylates. In some embodiments, suitable salts may include sodium, calcium, cesium, zinc, aluminum, magnesium, potassium, strontium, silicon, lithium, chlorides, bromides, carbonates, iodides, chlorates, bromates, formates, nitrates, sulfates, phosphates, oxides, fluorides and combinations of these. In some particular embodiments, brine may be used in the aqueous phase. Without being bound by any particular theory, brine may be used to create osmotic balance between the drilling fluid and the subterranean formation.

In some embodiments, the drilling fluid may contain from 10 volume percent (vol %) to 70 vol % of the aqueous phase based on the total weight of the drilling fluid. In some embodiments, the drilling fluid may contain from 28 pounds per barrel (lb/bbl) to 630 lbs/bbl, such as from 30 to 600 lbs/bbl, from 50 to 500 lbs/bbl, from 100 to 500 lb/bbl, 200 to 500 lbs/bbl, or 300 to 600 lbs/bbl of the aqueous phase. A barrel is equivalent to roughly 42 U.S. gallons or 159 liters.

The oleaginous phase of the drilling fluid may comprise oil, such as natural or synthetic liquid oil, and derivatives or fractions of these. The oleaginous phase may be or may contain diesel oil, mineral oil, aromatic hydrocarbons, hydrogenated or non-hydrogenated olefins such as poly-alpha-olefins, alpha-olefins, linear and branched olefins, poly-diorgonosiloxanes, silxoanes, organosiloxanes, esters of fatty acids, straight chain, branched or cyclical alkyl ethers of fatty acids, or combinations of any of these. The oleaginous phase may contain esters, ethers, acetals, dialkylcarbonates, or combinations of any of these. In some embodiments, the oleaginous phase may contain mineral oils, paraffin, and oils derived from plants, such as safra oil, for example.

The drilling fluid may contain from 30 vol % to 95 vol % of the oleaginous phase based on the total weight of the drilling fluid. The drilling fluid may contain from 28 lb/bbl. to 810 lb/bbl of the oleaginous phase based on the total weight of the drilling fluid, such as from 30 to 800 lb/bbl, from 50 to 800 lb/bbl, from 75 to 800 lb/bbl, or from 100 to 800 lb/bbl. In some embodiments, the drilling fluid may contain from 200 to 800 lb/bbl, or 300 to 600 lb/bbl, or 500 to 810 lb/bbl of the oleaginous phase.

The drilling fluid may, in some embodiments, be an invert (water-in-oil) emulsion in which water droplets (aqueous phase as the dispersed phase) are suspended in an oil-based fluid (oleaginous phase as the continuous phase). While water-based drilling fluids can be environmentally friendly and cost-efficient, they corrode metal tools and disintegrate clays and salts in the drilled zones, making them an undesirable choice for many applications. Oil-based fluids are more compatible with tooling, but are also more costly and cause concerns with handling, as discharging whole fluid or cuttings generated with oil-based fluids is not permitted in many offshore-drilling areas. An invert emulsion fluid may allow the benefits of both water-based and oil-based fluids to be utilized. However, as oil and water are incompatible, the oil and water phases may need to be mechanically mixed under increased shear to form the emulsion, which may be aided by the presence of suitable emulsifiers.

Embodiments of the disclosure are also directed to methods of producing drilling fluids, for example, an invert emulsion, by mixing an aqueous phase, an oleaginous phase, and N-hydroxyalkylated polyamine. In some embodiments, the method may include mixing the aqueous phase, the oleaginous phase, and the N-hydroxyalkylated polyamine under shear. The aqueous phase, the oleaginous phase, and the N-hydroxyalkylated polyamine may be mixed in accordance with the API (American Petroleum Institute) 13A: *Specification for Drilling-Fluid Materials*. For example, the additives may be mixed at room temperature utilizing a multi-mixer running at API specified speed 11,500 rpm (+/−300 rpm).

The drilling fluid may contain from 0.01 wt % to 20 wt % of the N-hydroxyalkylated polyamine based on the total weight of the drilling fluid. The drilling fluid may contain from 0.02 lb/bbl to 180 lb/bbl of the N-hydroxyalkylated polyamine based on the total weight of the drilling fluid, such as from 0.02 to 150 lb/bbl, or from 0.05 to 150 lb/bbl. In some embodiments, the drilling fluid may contain from 0.1 to 150 lb/bbl, or from 0.1 to 100 lb/bbl, or from 1 to 100 lb/bbl of the N-hydroxyalkylated polyamine.

In some embodiments, the drilling fluid may contain at least one additive other than the N-hydroxyalkylated polyamine. The one or more additives may be any additives known to be suitable for drilling fluids. As non-limiting examples, suitable additives may include emulsifiers, weighting agents, fluid loss control agents, lost circulation control agents, other surfactants, antifoaming agents, supplemental emulsifiers, weighting agent, fluid loss additives, other viscosity adjusters, an alkali reserve, specialty additives, and combinations of these.

In some embodiments, the drilling fluid may contain from 0.01 wt % to 20 wt % of the one or more additives based on the total weight of the drilling fluid. The drilling fluid may contain from 0.02 lb/bbl to 180 lb/bbl of the one or more additives based on the total weight of the drilling fluid, such as from 0.02 to 150 lb/bbl, or from 0.05 to 150 lb/bbl. In some embodiments, the drilling fluid may contain from 0.1 to 150 lb/bbl, or from 0.1 to 100 lb/bbl, or from 1 to 100 lb/bbl of the one or more additives.

As previously mentioned, in some embodiments, the drilling fluid of the present disclosure may not contain clay, or may contain reduced amounts of clay, while still producing a viscous drilling fluid. In some embodiments, the drilling fluid may contain less than or equal to 0.5 lb/bbl of clay, such as less than or equal to 0.1 lb/bbl, 0.05 lb/bbl, or 0.02 lb/bbl. In some embodiments, the clay is treated with hydrophobicizing agents to become lyophilic. Such clays are referred to as organophilic clays and are added to drilling fluids which have oleaginous phase as the continuous phase.

Embodiments of the disclosure may also relate to methods of using the drilling fluid. The drilling fluid may be in accordance with any of the embodiments previously described. In some embodiments, the drilling fluid may be pumped into a subterranean formation. Pumping may involve injecting the drilling fluid into the subterranean formation, which in some embodiments, may be a well. The drilling fluid may be recirculated from the wellbore to surface, passed through filters to remove solids such as drill cuttings, reconditioned with suitable additives to adjust rheology, and circulated back into the wellbore for further drilling.

While embodiments of the drilling fluid may be used in hydraulic fracturing processes in the oil and gas industry, the drilling fluid may also be used in other industries. For instance, the fluid may, in some embodiments, be used to stimulate groundwater wells, to precondition or induce rock cave-ins for mining operations, to dispose of waste by injecting it deeply into rock, to measure stresses in the Earth's crust, for electricity generation in enhanced geothermal systems, and to increase injection rates for the geologic sequestration of $CO_2$.

EXAMPLES

To demonstrate the improved rheological properties of the drilling fluids containing N-hydroxyalkylated polyamines, several tests were performed comparing a drilling fluid with N-hydroxyalkylated polyamine rheology modifier (Example 1) versus a drilling fluid containing a commercial dimer diamine rheology modifier (Comparative Example 1) and a drilling fluid containing a commercial dimer acid rheology modifier (Comparative Example 2). The formulations for these drilling fluid examples are provided in Tables 1. Each drilling fluid example is the same with the exception of the rheology modifier composition.

TABLE 1

Composition for Comparative Examples 1 and 2 and Example 1

| Component | Amount |
| --- | --- |
| Diesel | 0.62 barrels (bbl) |
| GELTONE ® | 2 pounds per barrel (lb/bbl) |
| Lime | 6 lb/bbl |
| VERSAMUL | 8 lb/bbl |
| VERSACOAT | 4 lb/bbl |
| Water | 0.14 bbl |
| $CaCl_2$ | 21.2 lb/bbl |
| VERSATROL | 4 lb/bbl |
| Barite | 224 lb/bbl |
| REV DUST | 2 lb/bbl |
| Rheology modifier | 2 lb/bbl |

In Table 1, "bbl" stands for barrels, equivalent to roughly 42 U.S. gallons or 159 liters. Likewise, "lb/bbl" stands for pounds per barrel. GELTONE® V refers to an organophilic clay viscosifier, commercially available from Halliburton (Ontario, Calif.). Lime refers to calcium oxide, CaO. VERSAMUL refers to a multi-purpose emulsifier, commercially available from Schlumberger (Houston, Tex.). VERSACOAT refers to a wetting agent and secondary emulsifier, also commercially available from Schlumberger (Houston, Tex.). $CaCl_2$ refers to calcium chloride, which can be used to provide osmotic wellbore stability. VERSATROL refers to an asphalt used for high-temperature high-pressure (HTHP) filtration control, commercially available from Schlumberger (Houston, Tex.). Barite refers to a dense sulfate mineral having the formula $BaSO_4$, commonly used to add weight to drilling fluids. REV DUST refers to a friction reducing material composted of small dust-like particles of calcium montmorillonite clay, commercially available from Milwhite, Inc. (Brownsville, Tex.).

Comparative Example 1 included Priamine™ 1074, a commercial dimer diamine produced by Croda International PLC, as its Rheology Modifier.

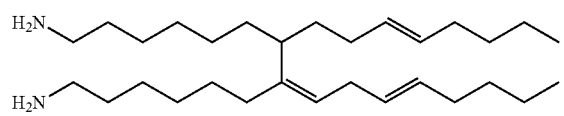 [SMILES: CCCC/C=C/C/C=C(/CCCCCCN)C(CC/C=C/CCCC)CCCCCCN]

The Example 1 N-hydroxyalkylated polyamine was produced by reacting the Priamine™ 1074 with ethylene oxide. The commercial dimer diamine (Priamine 1074) was added to a 500 milliliter (mL) Parr reactor which was sealed and subsequently sparged with nitrogen for one hour at 120° C. to drive out any oxygen and water from the solution. The system was then sealed and bled to atmospheric pressure. Ethylene oxide was added via a swagelock quick connect from a lecture bottle containing 99.9% ethylene oxide. The mass of oxide was determined by subtraction of the tared lecture bottle. As ethylene oxide was added, the pressure in the vessel increased, and the ethylene oxide reacted and was converted from a gas phase into a liquid phase, causing a drop in pressure. Ethylene oxide was added until the theoretical maximum of 4 moles of ethylene oxide to one mole of priamine or a priamine to ethylene oxide weight ratio of 1:0.36 was reached. When other amine amines are used as reactants, the theoretical maximum of hydroxyethylating agent to the primary amine groups in the molecule is a molar ratio of 2:1. Then the reaction was allowed to continue for 1 hour before cooling down. Any excess pressure was bled off through a caustic solution to scrub any potential excess ethylene oxide. As shown in the following reaction mechanism, the amines of the dimer diamine reacted by epoxide ring opening to form the N-hydroxyalkylated polyamine.

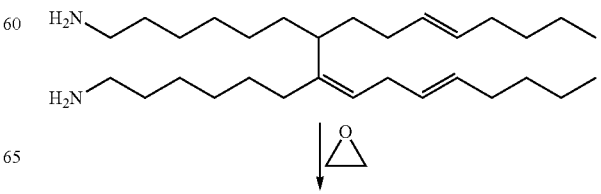

-continued

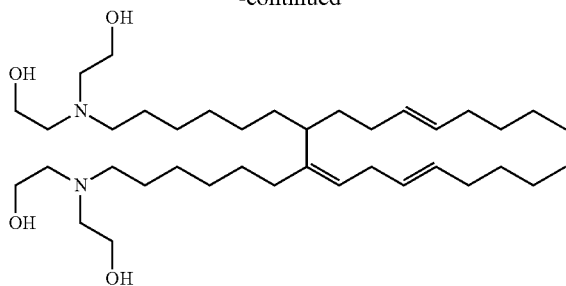

Comparative Example 2 included a UNIDYME™ 18 dimer diacid from Kraton Corporation as the Rheology Modifier. The other additives of the drilling fluid are provided in Table 1. The drilling fluids (Comparative Examples 1 and 2 and Example 1) were mixed in accordance with the API 13A: *Specification for Drilling-Fluid Materials*. Specifically, the additives were mixed at room temperature utilizing a multi-mixer running at API specified speed 11,500 rpm (+/−300 rpm). The additives were added at room temperature and pressure, one at a time, allowing 5 minutes of mixing between each addition. The only exception is that water and $CaCl_2$ were premixed and added as a brine to the drilling fluid.

Example 1 and Comparative Examples 1 and 2 were evaluated based on electrical stability, gel strength, and shear stress, which were all measured according to industry standard API 13B-2: *Recommended Practice for Field Testing Oil-Based Drilling Fluids*. For the electrical stability (ES) test, an electrical field is applied and the voltage recorded is the voltage required to complete the circuit, which can only occur when the emulsion breaks. Thus, the greater the voltage, the stronger the emulsion. Electrical stability was measured using a Fann 23 electrical stability meter before and after aging 16 hours at a temperature of 350° F. The 10 second and the 10 minute gel strengths were measured using a Fann 35 rotational coutte type viscometer without rotation (static conditions). The shear stress values were measured at 3 rpm and various temperatures using a Fann 77, which is a high temperature, high pressure (HTHP) rotational coutte type rheometer.

TABLE 2

Rheological Properties of the Drilling Fluids

| Property | Example 1 | Comparative Example 1 | Comparative Example 2 |
| --- | --- | --- | --- |
| Electrical stability before aging | 1068 V | 747 V | 299 V |
| Electrical stability after aging (350° F. for 16 hours) | 564 V | 380 V | 157 V |
| Gel Strength-10 seconds | 8 lb$_f$/100 ft$^2$ | 7 lb$_f$/100 ft$^2$ | 2 lb$_f$/100 ft$^2$ |
| Gel Strength-10 minutes | 11 lb$_f$/100 ft$^2$ | 19 lb$_f$/100 ft$^2$ | 3 lb$_f$/100 ft$^2$ |
| Shear Stress at 3 rpm and 150° F. | 8 lb$_f$/100 ft$^2$ | 9 lb$_f$/100 ft$^2$ | 1 lb$_f$/100 ft$^2$ |
| Shear Stress at 3 rpm and 200° F. | 7 lb$_f$/100 ft$^2$ | 7 lb$_f$/100 ft$^2$ | 1 lb$_f$/100 ft$^2$ |
| Shear Stress at 3 rpm and 250° F. | 6 lb$_f$/100 ft$^2$ | 5 lb$_f$/100 ft$^2$ | 1 lb$_f$/100 ft$^2$ |
| Shear Stress at 3 rpm and 350° F. | 7 lb$_f$/100 ft$^2$ | 3 lb$_f$/100 ft$^2$ | 2 lb$_f$/100 ft$^2$ |

In Table 2, V stands for volts, and lb$_f$ stands for pounds of force, and lb$_f$/ft$_2$ stands for pounds of force per square foot. As shown in Table 2, Example 1 had greater electrical stability before and after aging relative to Comparative Examples 1 and 2. This demonstrates that the N-hydroxyalkylated polyamine yields a more stable invert emulsion drilling fluid 1 than the comparatives. Moreover, the 10 sec gel strength for Example 1 (N-hydroxyalkylated polyamine rheology modifier) was similar to the Comparative Example 1 (dimer diamine); however, Comparative Example 1 showed a much larger increase at 10 minutes relative to Example 1. This large increase is undesirable as it can indicate a solid (gel) structure buildup in the drilling mud. Also, the shear stress values at the 3 rpm reading shows that as temperature increases, Comparative Examples 1 and 2 (the dimer diamine and the dimer acid, respectably) had significantly lower shear stress values, indicating a loss of rheological properties. In contrast, Example 1 (the N-hydroxyalkylated polyamine) still showed relatively stable shear stress as the temperature increased.

It should be apparent to those skilled in the art that various modifications and variations may be made to the embodiments described within without departing from the spirit and scope of the claimed subject matter. Thus, it is intended that the specification cover the modifications and variations of the various embodiments described within provided such modification and variations come within the scope of the appended claims and their equivalents.

It is noted that one or more of the claims utilize the term "where" as a transitional phrase. For the purposes of defining the present technology, it is noted that this term is introduced in the claims as an open-ended transitional phrase that is used to introduce a recitation of a series of characteristics of the Formula and should be interpreted in like manner as the more commonly used open-ended preamble term "comprising."

The invention claimed is:

1. An N-hydroxyalkylated polyamine of Formula (I):

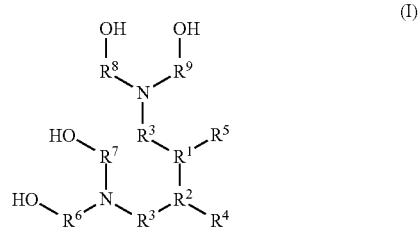

where:
  $R^1$ and $R^2$ are independently a —C or —CH group;
  $R^3$ is an aliphatic hydrocarbyl;
  $R^4$ and $R^5$ are independently acyclic hydrocarbyls, or $R^1$, $R^2$, $R^4$, and $R^5$ are covalently connected to form an unsaturated cyclic hydrocarbyl, wherein the unsaturated cyclic hydrocarbyl is substituted with one or more of an alkyl, aminoalkyl, aminoalkoxy, hydroxyl, alkoxyl, alkylthio, amino, halo, haloalkyl, silyl, phosphoryl, sulfonyl, saturated $C_2$-$C_{20}$ acyclic hydrocarbyls, or unsaturated $C_2$-$C_{20}$ acyclic hydrocarbyls; and
  $R^6$, $R^7$, $R^8$, and $R^9$ are independently acyclic hydrocarbyls or acyclic heterohydrocarbyls.

2. The N-hydroxyalkylated polyamine of claim 1, where $R^3$ is a saturated or unsaturated $C_2$-$C_{20}$ acyclic hydrocarbyl.

3. The N-hydroxyalkylated polyamine of claim 1, where at least one of $R^4$ and $R^5$ are unsaturated $C_2$-$C_{20}$ acyclic hydrocarbyls.

4. The N-hydroxyalkylated polyamine of claim 1, where the unsaturated cyclic hydrocarbyl is substituted with at least two acyclic hydrocarbyls.

5. The N-hydroxyalkylated polyamine of claim 1, where the unsaturated cyclic hydrocarbyl is substituted with at least one $C_2$-$C_{20}$ aminoalkoxy comprising two terminal hydroxyls.

6. The N-hydroxyalkylated polyamine of claim 1, where $R^1$, $R^2$, $R^4$ and $R^5$ form an unsaturated cyclic hydrocarbyl, wherein the unsaturated cyclic hydrocarbyl is selected from Formulas (III) to (XVII):

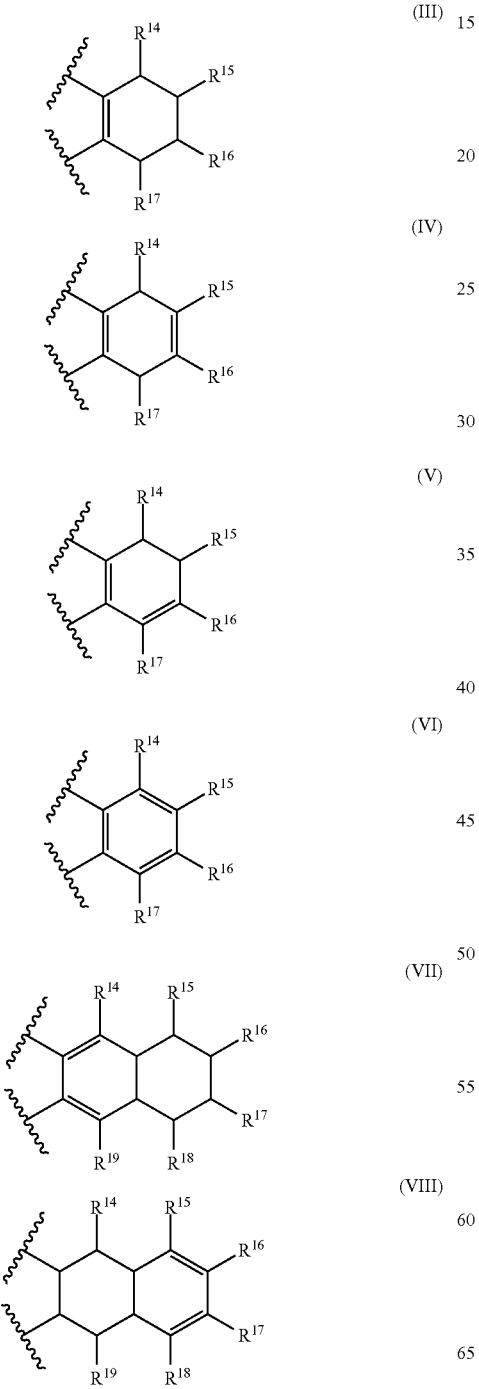

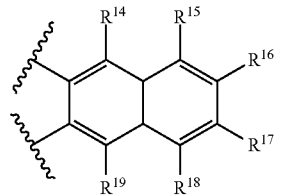

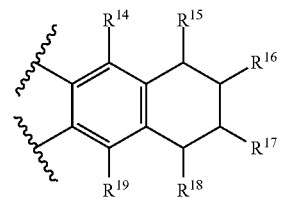

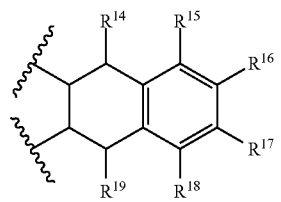

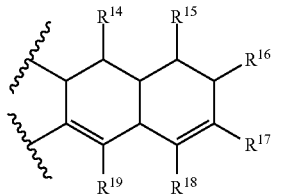

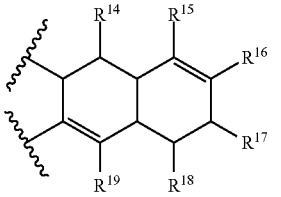

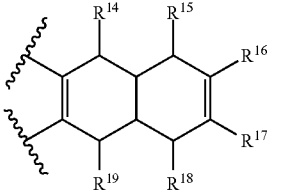

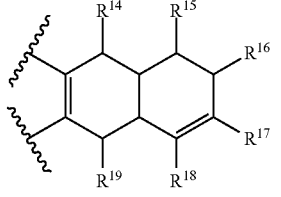

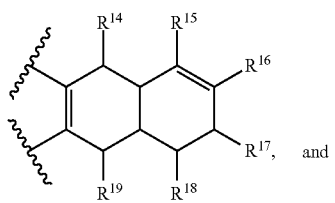
(XVI)

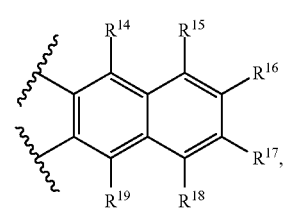
(XVII)

where $R^{14}$, $R^{15}$, $R^{16}$, $R^{17}$, $R^{18}$, and $R^{19}$ independently are H, alkyl, aminoalkyl, aminoalkoxy, hydroxyl, alkoxyl, alkylthio, amino, halo, haloalkyl, silyl, phosphoryl, sulfonyl, or combinations of these, and where at least one of $R^{14}$, $R^{15}$, $R^{16}$, $R^{17}$, $R^{18}$, and $R^{19}$ is not H.

7. A drilling fluid comprising:
an aqueous phase;
an oleaginous phase; and
an N-hydroxyalkylated polyamine of Formula (I):

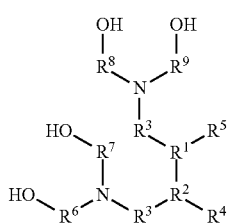
(I)

where:
$R^1$ and $R^2$ are independently a —C or —CH group;
$R^3$ is an aliphatic hydrocarbyl;
$R^6$, $R^7$, $R^8$, and $R^9$ are independently acyclic hydrocarbyls or acyclic heterohydrocarbyls; and
$R^1$, $R^2$, $R^4$ and $R^5$, form a cyclic hydrocarbyl, the cyclic hydrocarbyl being selected from Formulas (II) to (XVIII):

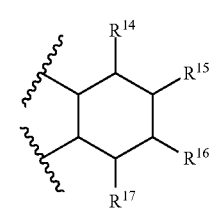
(II)

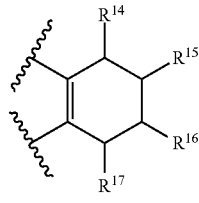
(III)

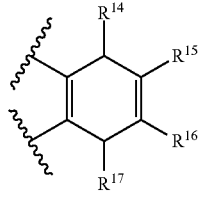
(IV)

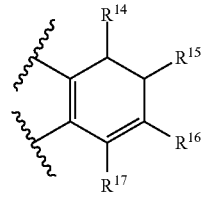
(V)

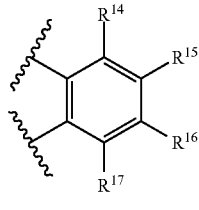
(VI)

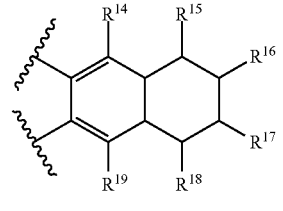
(VII)

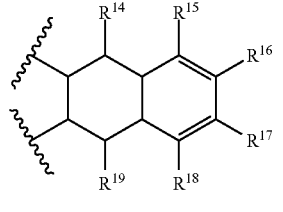
(VIII)

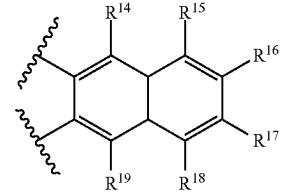
(IX)

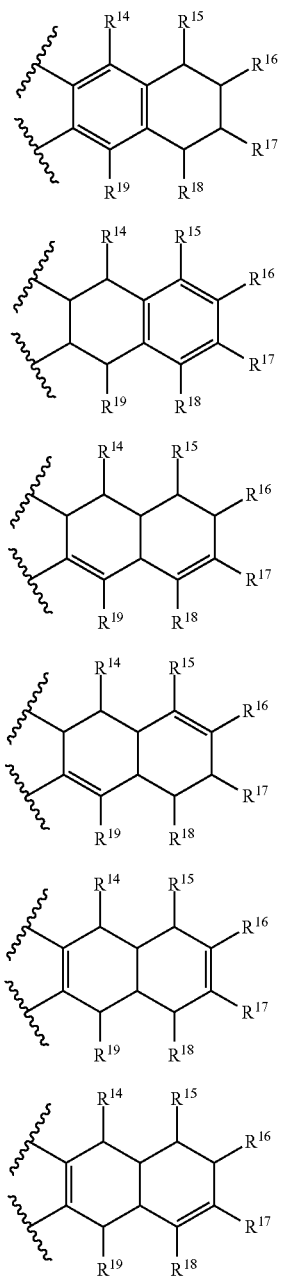

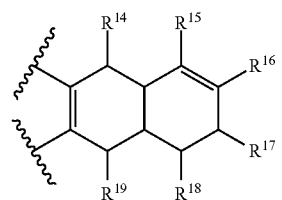

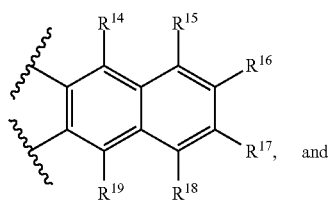

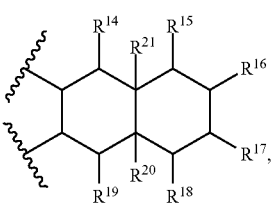

wherein, $R^{14}$, $R^{15}$, $R^{16}$, $R^{17}$, $R^{18}$, $R^{19}$, $R^{20}$, and $R^{21}$ independently are H, alkyl, aminoalkyl, aminoalkoxy, hydroxyl, alkoxyl, alkylthio, amino, halo, haloalkyl, silyl, phosphoryl, sulfonyl, or combinations of these.

8. The drilling fluid of claim 7, where $R^3$ is a saturated or unsaturated $C_2$-$C_{20}$ acyclic hydrocarbyl group.

9. The drilling fluid of claim 7, where the cyclic hydrocarbyl is substituted with one or more of alkyl, aminoalkyl, aminoalkoxy, hydroxyl, alkoxyl, alkylthio, amino, halo, haloalkyl, silyl, phosphoryl, sulfonyl, saturated $C_2$-$C_{20}$ acyclic hydrocarbyls, or combinations thereof.

10. The drilling fluid of claim 7, where the cyclic hydrocarbyl is substituted with at least one $C_2$-$C_{20}$ aminoalkoxy comprising two terminal hydroxyls.

11. The N-hydroxyalkylated polyamine of claim 1, where $R^4$ and $R^5$ are independently acyclic hydrocarbyls.

* * * * *

UNITED STATES PATENT AND TRADEMARK OFFICE
CERTIFICATE OF CORRECTION

PATENT NO. : 10,934,249 B2
APPLICATION NO. : 16/353607
DATED : March 2, 2021
INVENTOR(S) : Matthew Hilfiger and B. Raghava Reddy Page 1 of 1

It is certified that error appears in the above-identified patent and that said Letters Patent is hereby corrected as shown below:

In the Specification

In Column 4, Line(s) 50, after "$R^2$,", insert --$R^4$,--.

In Column 5, Line(s) 11, delete "$C_5$-$C_{30}$" and insert --$C_5$-$C_{10}$--, therefor.

In Column 5, Line(s) 24, after "unsaturated", delete ".".

In Column 15, Line(s) 55, delete "$R^5$ and $R^6$" and insert --$R^4$ and $R^5$--, therefor.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*